US010918566B2

(12) United States Patent
Herken et al.

(10) Patent No.: US 10,918,566 B2
(45) Date of Patent: *Feb. 16, 2021

(54) CHEST COMPRESSION BELT WITH BELT POSITION MONITORING SYSTEM

(71) Applicant: ZOLL Medical Corporation, Chelmsford, MA (US)

(72) Inventors: Ulrich R Herken, Medford, MA (US); Gary A Freeman, Waltham, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 309 days.

This patent is subject to a terminal disclaimer.

(21) Appl. No.: 15/891,639

(22) Filed: Feb. 8, 2018

(65) Prior Publication Data

US 2018/0228692 A1 Aug. 16, 2018

Related U.S. Application Data

(63) Continuation of application No. 14/452,014, filed on Aug. 5, 2014, now Pat. No. 9,925,114, which is a
(Continued)

(51) Int. Cl.
*A61H 31/00* (2006.01)
*A61N 1/04* (2006.01)
*A61H 11/00* (2006.01)

(52) U.S. Cl.
CPC ........... *A61H 31/00* (2013.01); *A61H 31/005* (2013.01); *A61H 31/006* (2013.01);
(Continued)

(58) Field of Classification Search
CPC .... A61H 31/00; A61H 31/005; A61H 31/008; A61H 31/006; A61H 2011/005;
(Continued)

(56) References Cited

U.S. PATENT DOCUMENTS

| 4,770,164 A | 9/1988 | Lach et al. |
| 4,928,674 A | 5/1990 | Halperin et al. |

(Continued)

FOREIGN PATENT DOCUMENTS

| CN | 201346293 Y | 11/2009 |
| CN | 201437005 U | 4/2010 |

(Continued)

OTHER PUBLICATIONS

Dahmen, Feedback Derived From 3D Accelerometers Used for Autonomous Correction of Chest Compression Movement in Cardiopulmonary Resuscitation Training, University of Twente 2 (2011).
(Continued)

*Primary Examiner* — Quang D Thanh
(74) *Attorney, Agent, or Firm* — ZOLL Medical Corporation

(57) ABSTRACT

An automated chest compression device for performing CPR, with distance sensors disposed on a compressing mechanism and on a structure fixed relative to the CPR patient, for determining inferior/superior movement of the compressing mechanism over the course of multiple compressions.

31 Claims, 10 Drawing Sheets

Related U.S. Application Data continuation of application No. 13/907,621, filed on May 31, 2013, now Pat. No. 8,795,209.

(60) Provisional application No. 61/654,642, filed on Jun. 1, 2012.

(52) U.S. Cl.
CPC ...... *A61H 31/008* (2013.01); *A61H 2011/005* (2013.01); *A61H 2031/002* (2013.01); *A61H 2031/003* (2013.01); *A61H 2201/0161* (2013.01); *A61H 2201/0173* (2013.01); *A61H 2201/0184* (2013.01); *A61H 2201/1215* (2013.01); *A61H 2201/1664* (2013.01); *A61H 2201/5007* (2013.01); *A61H 2201/5043* (2013.01); *A61H 2201/5046* (2013.01); *A61H 2201/5048* (2013.01); *A61H 2201/5058* (2013.01); *A61H 2201/5064* (2013.01); *A61H 2201/5084* (2013.01); *A61H 2201/5092* (2013.01); *A61H 2201/5097* (2013.01); *A61H 2205/083* (2013.01); *A61H 2230/04* (2013.01); *A61N 1/0492* (2013.01)

(58) Field of Classification Search
CPC ........ A61H 2031/002; A61H 2031/003; A61H 2201/0173; A61H 2201/5043; A61H 2201/5048; A61H 2205/083; A61H 2230/04; A61H 2201/5058; A61H 2201/0184; A61H 2201/0161; A61H 2201/1215; A61H 2201/1664; A61H 2201/5007; A61H 2201/5046; A61H 2201/5064; A61H 2201/5084; A61H 2201/5092; A61H 2201/5097; A61N 1/0492; A61N 1/39044

See application file for complete search history.

(56) References Cited

U.S. PATENT DOCUMENTS

| | | | |
|---|---|---|---|
| 5,738,637 A | 4/1998 | Kelly et al. | |
| 6,066,106 A | 5/2000 | Sherman et al. | |
| 6,142,962 A | 11/2000 | Mollenauer et al. | |
| 6,213,960 B1 | 4/2001 | Sherman et al. | |
| 6,390,996 B1 | 5/2002 | Halperin et al. | |
| 6,398,745 B1 | 6/2002 | Sherman et al. | |
| 6,616,620 B2 | 9/2003 | Sherman et al. | |
| 6,670,910 B2 | 12/2003 | Delcheccolo et al. | |
| 6,676,613 B2 | 1/2004 | Cantrell et al. | |
| 6,690,616 B1 | 2/2004 | Bahr et al. | |
| 6,827,695 B2 | 12/2004 | Palazzolo | |
| 6,951,546 B2 | 10/2005 | Palmer et al. | |
| 6,952,605 B1 | 10/2005 | Scarberry | |
| 7,108,665 B2 | 9/2006 | Halperin et al. | |
| 7,220,235 B2 | 5/2007 | Geheb et al. | |
| 7,270,639 B2 | 9/2007 | Jensen et al. | |
| 7,347,832 B2 | 3/2008 | Jensen et al. | |
| 7,354,407 B2 | 4/2008 | Quintana et al. | |
| 7,429,250 B2 | 9/2008 | Halperin et al. | |
| 7,569,021 B2 | 8/2009 | Sebelius et al. | |
| 7,602,301 B1 | 10/2009 | Stirling et al. | |
| 8,092,404 B2 | 1/2012 | Kelly et al. | |
| 8,795,209 B2 * | 8/2014 | Herken ................ | A61H 31/006 601/44 |
| 9,486,390 B2 | 11/2016 | Centen et al. | |
| 9,585,603 B2 | 3/2017 | Centen | |
| 9,925,114 B2 * | 3/2018 | Herken ................ | A61H 31/006 |
| 2001/0047140 A1 | 11/2001 | Freeman | |
| 2008/0097257 A1 * | 4/2008 | Stromsnes ........... | A61H 31/008 601/41 |
| 2008/0171311 A1 * | 7/2008 | Centen ................. | G16H 20/30 434/265 |
| 2011/0092864 A1 | 4/2011 | Woerlee et al. | |
| 2013/0218055 A1 | 8/2013 | Fossan | |

FOREIGN PATENT DOCUMENTS

| | | |
|---|---|---|
| CN | 102106779 A | 6/2011 |
| CN | 102164573 A | 8/2011 |
| CN | 202078515 U | 12/2011 |
| WO | WO2000027334 A2 | 5/2000 |
| WO | WO2002091905 | 11/2002 |
| WO | WO2004112683 A1 | 12/2004 |
| WO | WO2005037179 A1 | 4/2005 |
| WO | WO2012001541 A1 | 1/2012 |

OTHER PUBLICATIONS

Extended European Search Report dated Jan. 20, 2016 from European Patent Application No. 13796418.5.

Office Action dated Nov. 26, 2015 from Chinese Patent Application No. 201380040277.

\* cited by examiner

CHEST COMPRESSION BELT WITH BELT POSITION MONITORING SYSTEM

This application is a continuation of U.S. application Ser. No. 14/452,014, filed Aug. 5, 2014, which claims priority to U.S. application Ser. No. 13/907,621, filed May 31, 2013, now U.S. Pat. No. 8,795,209, which claims priority to U.S. Provisional Application 61/654,642 filed Jun. 1, 2012. All subject matter set forth and described in each of the above referenced applications is hereby incorporated by reference in its entirety.

FIELD OF THE INVENTIONS

The inventions described below relate to the field of CPR chest compression devices.

BACKGROUND OF THE INVENTIONS

Cardiopulmonary resuscitation (CPR) is a well-known and valuable method of first aid used to resuscitate people who have suffered from cardiac arrest. CPR requires repetitive chest compressions to squeeze the heart and the thoracic cavity to pump blood through the body. Artificial respiration, such as mouth-to-mouth breathing or a bag mask apparatus, is used to supply air to the lungs. When a first aid provider performs manual chest compression effectively, blood flow in the body is about 25% to 30% of normal blood flow. However, even experienced paramedics cannot maintain adequate chest compressions for more than a few minutes. Hightower, et al., *Decay In Quality Of Chest Compressions Over Time,* 26 Ann. Emerg. Med. 300 (September 1995). Thus, CPR is not often successful at sustaining or reviving the patient. Nevertheless, if chest compressions could be adequately maintained, then cardiac arrest victims could be sustained for extended periods of time. Occasional reports of extended CPR efforts (45 to 90 minutes) have been reported, with the victims eventually being saved by coronary bypass surgery. See Tovar, et al., *Successful Myocardial Revascularization and Neurologic Recovery,* 22 Texas Heart J. 271 (1995).

In efforts to provide better blood flow and increase the effectiveness of bystander resuscitation efforts, various mechanical devices have been proposed for performing CPR. In one variation of such devices, a belt is placed around the patient's chest and the belt is used to effect chest compressions. Our own patents, Mollenauer, et al., Resuscitation Device Having A Motor Driven Belt To Constrict/Compress The Chest, U.S. Pat. No. 6,142,962 (Nov. 7, 2000); Sherman, et al., CPR Assist Device with Pressure Bladder Feedback, U.S. Pat. No. 6,616,620 (Sep. 9, 2003); Sherman, et al., Modular CPR assist device, U.S. Pat. No. 6,066,106 (May 23, 2000); and Sherman, et al., Modular CPR assist device, U.S. Pat. No. 6,398,745 (Jun. 4, 2002), show chest compression devices that compress a patient's chest with a belt. Each of these patents is hereby incorporated by reference in their entirety. Our commercial device, sold under the trademark AUTOPULSE®, is described in some detail in our prior patents, including Jensen, Lightweight Electro-Mechanical Chest Compression Device, U.S. Pat. No. 7,347,832 (Mar. 25, 2008) and Quintana, et al., Methods and Devices for Attaching a Belt Cartridge to a Chest Compression Device, U.S. Pat. No. 7,354,407 (Apr. 8, 2008).

These devices have proven to be valuable alternatives to manual CPR, and evidence is mounting that they provide circulation superior to that provided by manual CPR, and also result in higher survival rates for cardiac arrest victims. The AUTOPULSE® CPR devices are intended for use in the field, to treat victims of cardiac arrest during transport to a hospital, where the victims are expected to be treated by extremely well-trained emergency room physicians. The AutoPulse® CPR device is uniquely configured for this use: All the components are stored in a lightweight backboard, about the size of a boogie board, which is easily carried to a patient and slipped underneath the patient's thorax. The important components include a compression belt, motor, drive shaft and drive spool, computer control system and battery.

Addressing another aspect of CPR, chest compression monitoring during the course of CPR is now possible with the Real CPR Help® technology marketed by ZOLL Medical Corporation. This technology is described in U.S. Pat. Nos. 6,390,996, 7,108,665, and 7,429,250, and includes the use of an accelerometer to measure accelerations of the chest and calculating the depth of each compression from the acceleration signal. The technology is used in ZOLL's Real CPR Help® compression depth monitoring system to provide real-time rate and depth CPR feedback for manual CPR providers. Commercially, it is implemented in ZOLL's electrode pads, such as the CPR-D•padz® electrode pads. It is also implemented for training use in the iPhone app PocketCPR®. The same technology can be provided in automatic CPR chest compression devices, such as ZOLL Circulation's AutoPulse® chest compression device, which is described in numerous patents issued to ZOLL Circulation such as U.S. Pat. No. 6,066,106 and its continuations. U.S. Pat. Nos. 6,390,996, 7,108,665, and 7,429,250 also propose use of compression depth monitoring in combination with an automatic constricting device described in U.S. Pat. No. 4,928,674, which is an inflatable vest operable to squeeze the chest of a patient repeatedly to provide CPR chest compressions.

The Real CPR Help® compression depth monitoring system provides valuable unambiguous feedback during manual CPR, because the accelerometer is fixed to the chest of the patient either because is it fixed to electrode pads that are fixed to the patient's chest with adhesive, or because it is fixed relative the CPR providers hands which the CPR provider maintains in the appropriate location over the sternum of the patient. Chest compression information that might be provided during automated CPR with the AutoPulse® device may be unambiguous, assuming that the compression belt used with the AutoPulse® device does not shift during the course of treatment. While this may be monitored visually by an EMT using the AutoPulse®, the system can be improved by providing some mechanism for determining compression depth in the case where the compression belt shifts up or down on the patient's chest during use.

During the course of automated chest compression using the AutoPulse® chest compression device, CPR providers using the device may be concerned about inferior/superior movement of the belt. The device may be operated for several minutes, including time moving the patient into an ambulance, transporting the patient to a hospital, and moving the patient from the ambulance and into a hospital emergency room. With all this movement, it is possible that the compression belt might move either upward toward the patient's shoulders (superiorly, relative to the patient), or downward toward the patient's abdomen (inferiorly, relative to the patient). None of the references discussed above provide a means for detecting horizontal displacement or non-uniformity in the downward movement of a compression component of an automated chest compression device.

SUMMARY

The devices and methods described below provide for continuous monitoring of the inferior/superior position of a compression belt of a CPR compression device and continuous monitoring of the uniformity or non-uniformity of the downward movement of a compression belt. In one system described below, this is accomplished with a compression belt fitted with markers, which may be active signal emitters or passive signal reflectors, together with a plurality of signal detectors on a structure which is fixed relative to the patient (or, conversely, markers fixed relative to the patient in combination with signal detectors secured on the belt). In reference to the AutoPulse®, which uses a load distributing panels as components of a compression belt (now commonly referred to as a load distributing band) that is disposed over the chest of the patient during use, the markers or signal detectors may be disposed on the load distributing panels.

Movement of the belt-mounted component is tied to movement of the load distributing band or a portion of the load distributing band. Assuming that the fixed components (the housing or a separate support gantry) are held fixed relative to the patient's main mass (but not the chest components (sternum, anterior portions of the ribs) that are compressed by the compression belt), anterior/posterior movement of the load distributing band relative to the main mass of the patient, and inferior/superior movement (up and down, relative to the patient's body), can be detected and measured.

Anterior/posterior movement can be measured to determine depth of compression, and that measurement can be used to confirm proper compression and/or adjust compressions accomplished automatically by the CPR compression device. Superior/Inferior movement can be measured to confirm proper positioning of the compression belt or load distributing panels of the belt. Detection of inferior/superior movement, or lack of movement, can be used to determine improper placement, or confirm proper placement, of the compression belt or load distributing panels along the superior/inferior axis of the patient.

The detector/emitter system can work on several principles. Such detectors may be ultrasonic distance sensors, with corresponding markers comprising reflective surfaces, optical sensors, RFID sensors, or magnetic sensors. Using two detectors space apart from each other, and basic triangulation, the relative location of the belt-mounted component vis-à-vis the fixed components can be determined. A computer control system can be used in the conjunction with the emitter/detector system to calculate the location of the belt-mounted component vis-à-vis the fixed components, and determine desired and undesired movement of the compression belt. Proper depth of compression, inadequate or excessive compression, and inferior/superior slippage of the compression belt or load distributing panels, and even changes of the patient's chest caused by the compressions can be detected. In addition, spontaneous chest movements, or movements cause by ventilation, can be identified and measured.

A second system and method described below provides for continuous monitoring of the inferior/superior position of a compression belt of a CPR compression device and continuous monitoring of the uniformity or non-uniformity of the downward movement of a compression belt using a compression belt fitted with one or more accelerometers operable to detect horizontal movement of the compression belt, and a microprocessor or control system which interprets signals from the accelerometer(s) to determine horizontal movement of the belt. In reference to the AutoPulse®, which uses load distributing panels as components of a compression belt that is disposed over the chest of the patient during use, accelerometers may be disposed on the load distributing panels.

Movement of the belt-mounted accelerometer is tied to movement of the load distributing band or a portion of the load distributing band. Assuming that the fixed components are held fixed relative to the patient's main mass (but not the chest components that are compressed by the compression belt), anterior/posterior movement of the load distributing band relative to the main mass of the patient, and inferior/superior movement (up and down, relative to the patient's body), can be detected and measured. Anterior/posterior movement can be measured to determine depth of compression, as proposed in U.S. Pat. No. 6,390,996 and that measurement can be used to confirm proper compression and/or adjust compressions accomplished automatically by the CPR compression device. In addition, superior/inferior movement can be measured to confirm proper positioning of the compression belt or load distributing band. Detection of inferior/superior movement, or lack of movement, can be used to determine improper placement, or confirm proper placement, of the compression belt or load distributing band along the superior/inferior axis of the patient. In addition, anterior/posterior movement can be measured to confirm uniform downward motion of the compression belt or load distributing band. Detection of uniform anterior/posterior movement, or non-uniform anterior/posterior movement, can be used to confirm proper downward movement, or determine improper downward movement, of the compression belt or load distributing band.

With the information gained regarding the position of the belt-mounted component, the position of the belt and depth of compressions caused by the belt are calculated by the control system. The operation of the chest compression belt can be modified in response to the information. The compression belt operation can be adjusted, in response to the information gained. For example, the system may interrupt compressions if significant slippage is detected, and/or notify an EMT or other CPR provider that the compression belt has slipped out of place. The system may also be used to detect changes in chest compliance (which might be caused by airway blockage, natural remodeling of the chest over the course of treatment, or iatrogenic injury) and notify the CPR provider of significant changes. The system may also be used to control the chest compression belt operation so as to reach a specified depth of compression, or to interrupt compressions if ventilation or natural respiration is reflected in the position data.

The inventions described above can be used to perform CPR with parameters which vary according to the patient's shape, as determined by the distance sensors. The distance sensors can be used to determine the size and shape of the patient's chest, and the control system can then alter the compression depth to account for differing physiology such as flat or barrel chested patients. The distance sensors and/or the accelerometers, combined with measurements of chest compliance or resilience, can be used by the control system to determine the relationship between the compression depth achieved and the force applied to the chest, and adjust the target compression depth when the relationship suggest that chest compliance has increased due to breakage of the patient's ribs.

DETAILED DESCRIPTION OF THE INVENTIONS

Figure 1:
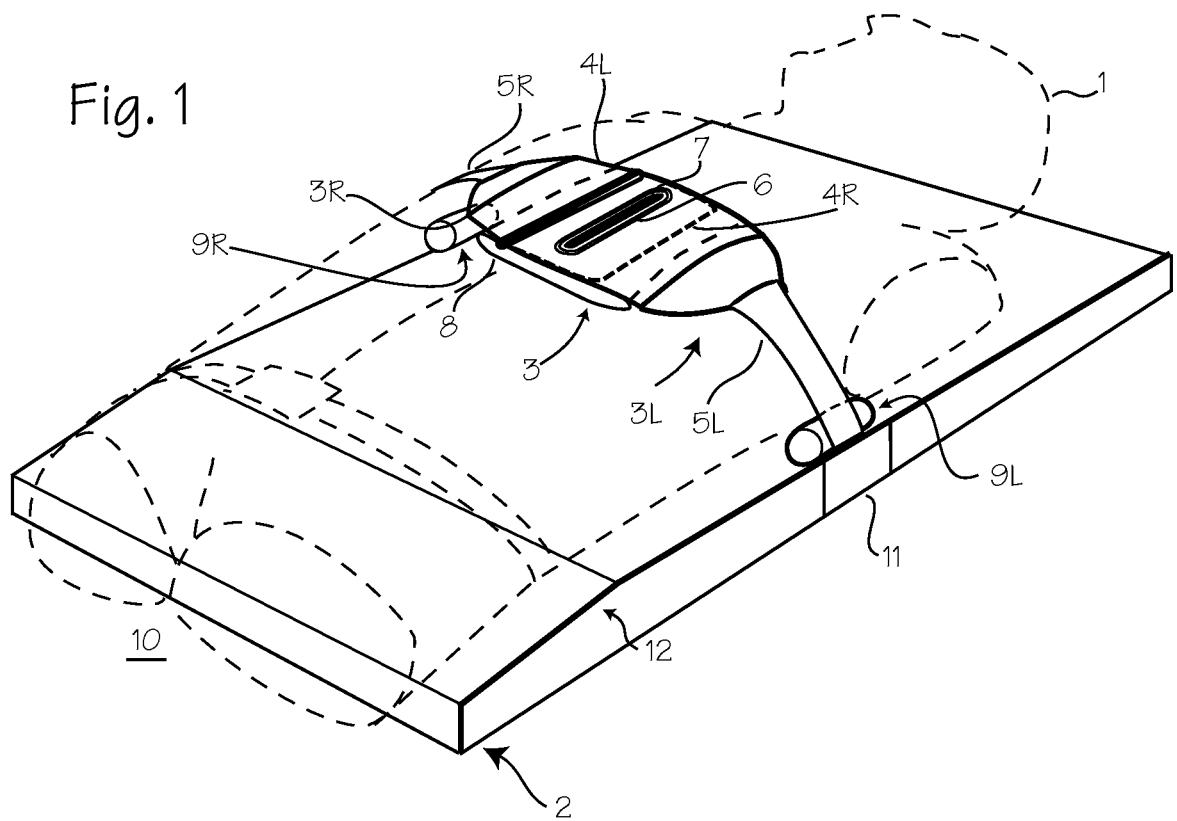
FIG. 1 shows a chest compression belt fitted on a patient.
Figure 2:
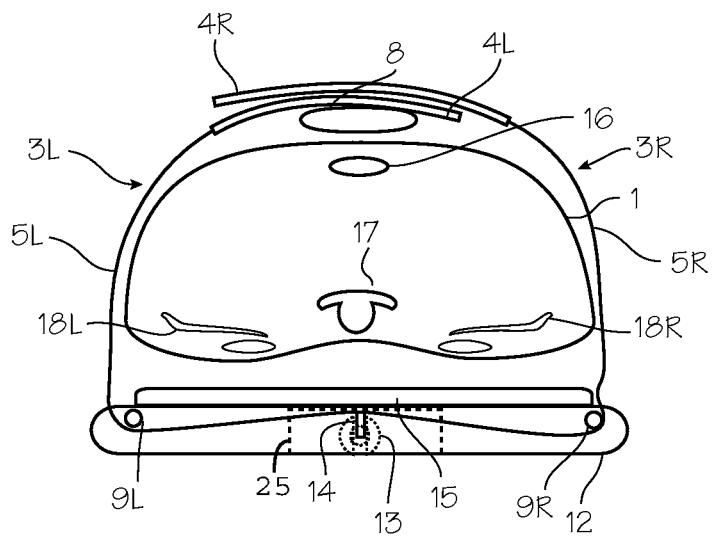
FIG. 2 is a schematic cross section of the chest compression device of FIG. 1.

FIGS. 1 and 2 illustrate the chest compression device, similar to the AutoPulse® CPR chest compression device, fitted on a patient 1. A chest compression device 2 applies compressions with the belt 3, which has a right belt portion 3R and a left belt portion 3L, including load distributing panels 4R and 4L designed for placement over the anterior surface of the patient's chest while in use, and tensioning portions which extend from the load distributing portions to a drive spool, shown in the illustration as narrow pull straps 5R and 5L. (The entirety of the compression belt is referred to as a "load distributing band" in the art.) The right belt portion and left belt portion are secured to each other with hook and loop fasteners and aligned with the eyelet 6 and protrusion 7. A bladder 8 is disposed between the belt and the chest of the patient. The narrow pull straps 5R and 5L of the belt are spooled onto a drive spool located within the platform (shown in FIG. 2) to tighten the belt during use, passing first over laterally located spindles 9L and 9R. The chest compression device 2 includes a platform 10 and a compression belt cartridge 11 (which includes the belt). The platform includes a housing 12 upon which the patient rests. Means for tightening the belt, a processor and a user interface are disposed within the housing. In the commercial embodiment of the device, the means for tightening the belt includes a motor, a drive train (clutch, brake and/or gear box) and a drive spool upon which the belt spools during use.

FIG. 2 is a schematic cross section of the device of FIG. 1, installed on a patient 1. The components include the compression belt 3L and 3R, the load distribution portions of the belt 4L and R, the narrow strap portions 5L and R, the bladder 8, the spindles 9L and R. The drive spool 13 and the spline 14 which fixes the belt to the drive spool are located within the housing 12, as is a motor and computer control system which operate to drive the drive spool to spool the belt, thereby tightening the belt about the chest and thorax of the patient and a resuscitative rate to accomplish CPR. A load plate 15 is disposed on the platform (the upper surface of the housing). The anatomical landmarks shown in this Figure include the sternum 16, the spine 17, and the right and left scapula 18R and 18L of the patient. Referring to the landmarks, the chest compression band is wrapped around the patient such that the load distributing portions are located on the chest (that is, the anterior surface or portion of the thorax), over the sternum, with the narrow strap portions descending from the load distributing portions to wrap around the lateral spindles and thence run to the drive spool. The lateral spindles are spaced laterally from the medial centerline of the device so that they are disposed under, or lateral to, the scapulae of the typical patient, so that tightening of the compression band results in anterior/posterior compression of the chest. In use, the patient must remain fixed relative to the housing: That is, some anatomical parts of the patient must remain in substantially fixed relation to the housing while the sternum is compressed toward the spine. In practice, we find that the spine and scapula remain fixed, or nearly fixed, relative to the platform while the sternum and anterior portions of the thorax are compressed downwardly toward the spine, the scapula, and the housing.

Our experience with the belt suggests that it is desirable to monitor the position of the belt during CPR. Our compression depth monitor, describe in our Patent U.S. Pat. Nos. 6,390,996, 7,108,665, and 7,429,250, and commercialized under the Real CPR Help® trademark, can be used to provide feedback regarding the depth of compressions, which is a critical parameter for CPR. However, it is desirable to automatically detect slippage of the belt along the inferior/superior axis of the system, which would indicate that the belt has slipped up or down on the patient, or that the patient has moved or changed shape. Slipping can be caused by the interaction of forces applied by belt on the patient. Shape changes that effect the application of CPR can occur as a result of natural remodeling of the chest during the course of treatment. The system described in relation to FIGS. 3 and 4 can provide this information, and can also provide information regarding the inferior/superior motion of the compression belt.

Figure 3:
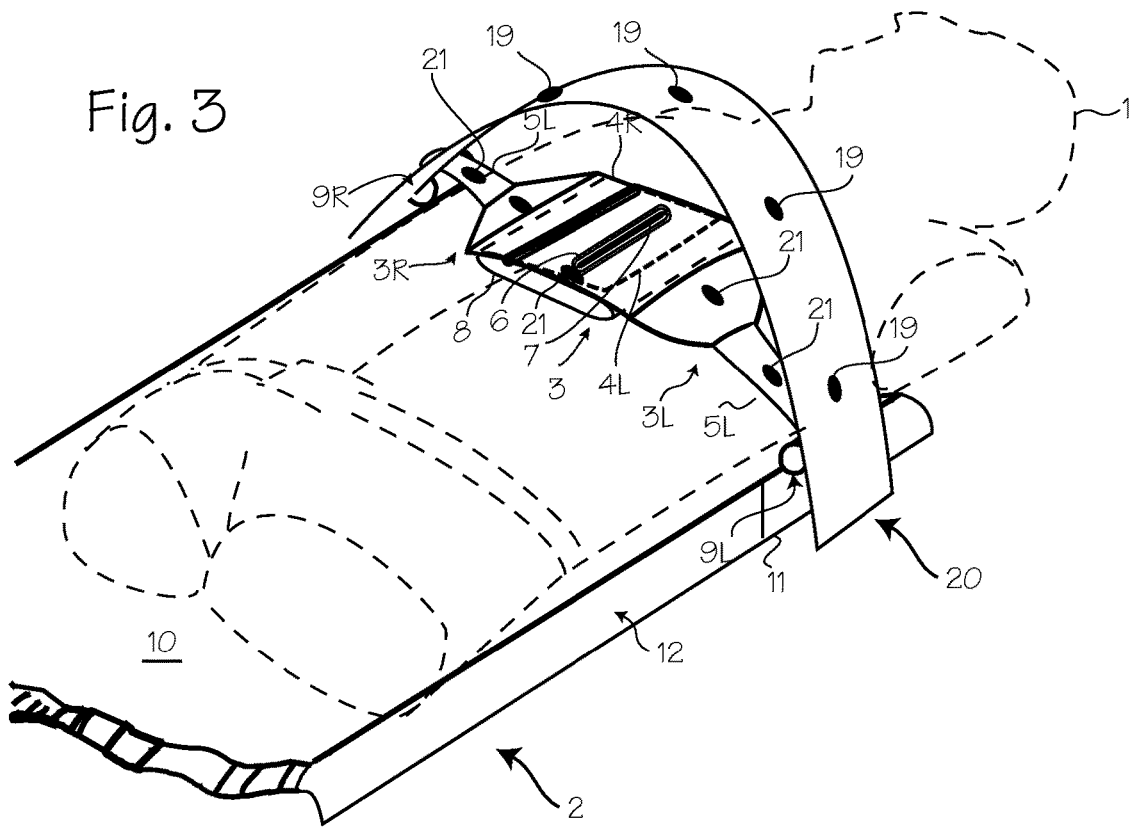
FIG. 3 shows a chest compression belt fitted on a patient, with a pair of emitter/detector arrays disposed about the chest compression device.
Figure 4:
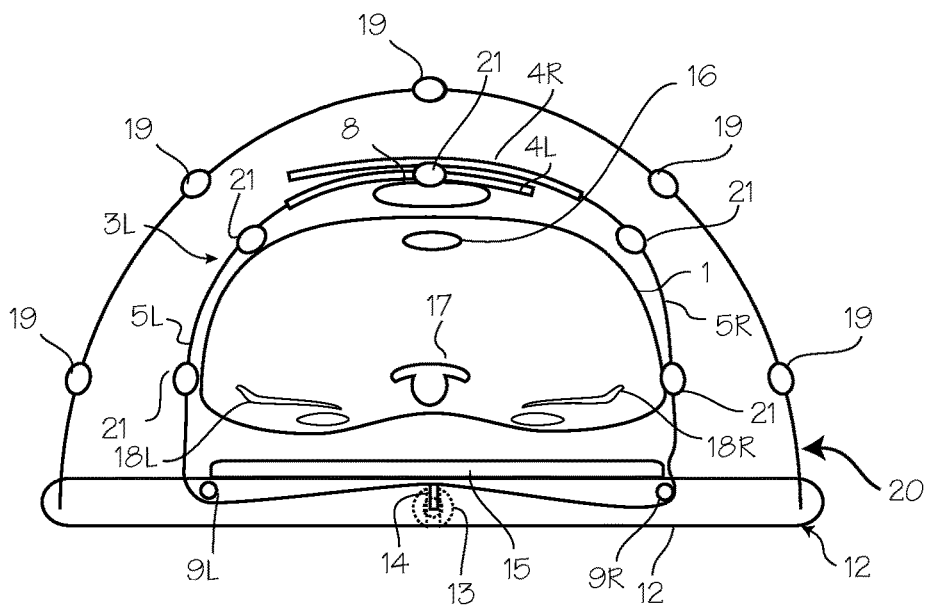
FIG. 4 is a schematic cross section of the chest compression device of FIG. 3.

As shown in FIGS. 3 and 4, and array assembly of emitter/detectors components is disposed about the patient, over the compression belt, and an array of detector/emitter components is arranged on the compression belt. The array assembly includes multiple emitter/detectors 19 arranged on a support structure 20 over the patient and the compression belt. The support structure of FIGS. 3 and 4 is sized and dimensioned to fit over the chest of the patient, over the compression belt, and may be fixed to the housing of the compression device. A second array assembly may be made up of the compression belt itself, along with multiple emitter/detectors 21 disposed on the belt. One or both of the sensor arrays may be operably connected to a computer (of any form) which may control operation of the emitter/detector components, accept signals provided from the emitter/detector components, analyze the signals and calculate from those signals the position of the emitter/detector components on the compression belt. The computer may be part of, or separate from, the computer that directly controls the CPR compression device. Depending on the emitter/detector technology, a second array may be unnecessary, and the desired distance measurements can be accomplished with a single array mounted on the support structure or the belt. Where, for example, ultrasonic distance sensors are used to implement the system, the emitter/detectors 21 can be replaced with detectable markers, or ultrasonic reflectors. Where, for example, optical sensors are used, the laser and camera components may be mounted on the gantry, and markers (reflectors) may be disposed on the belt (the belt itself may serve as the reflective surface).

Figure 5:
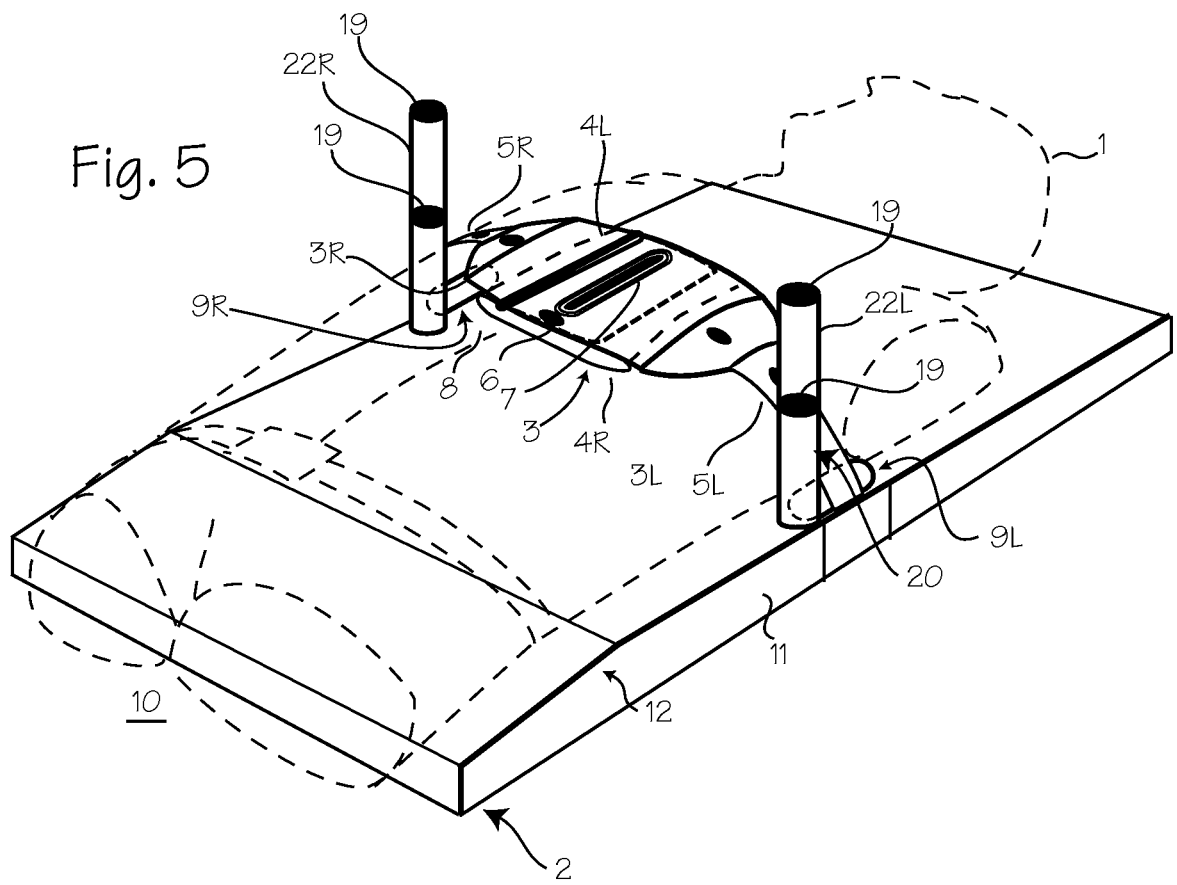
FIG. 5 is a schematic cross section of a chest compression device similar to that of FIG. 3, with one array disposed on posts disposed on the chest compression device.
Figure 6:
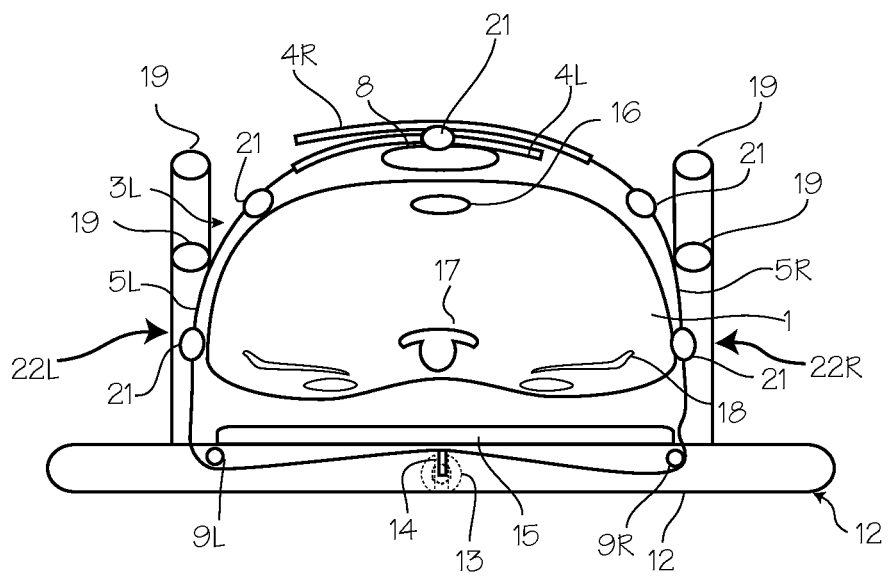
FIG. 6 is a schematic cross section of the chest compression device of FIG. 5.

The support structure may take various forms suitable for holding the emitter/detectors 19 spatially fixed relative to the housing of the compression device. FIG. 5 illustrates a chest compression device similar to that of FIG. 3, with one array disposed on posts disposed on the chest compression device. FIG. 6 is a schematic cross section of the chest compression device of FIG. 5. The compression device components include the housing 12, the compression belt 3L and 3R, the load distribution portions of the belt 4L and R, the narrow strap portions 5L and 5R, the bladder 8, the spindles 9L and R illustrated previously. The emitter/detectors 19 are disposed on support structure comprising posts 22L and 22R. The posts are mounted on the housing 12, extending vertically upwardly from the housing, on either side of the patient, in the area corresponding to the axillae of the patient when the device is installed on a patient. The mechanical posts may be approximately 6 inches (15 cm) in height and 1 inch (2.5 cm) in diameter. During positioning of the patient on the housing 12, the patient is positioned such that the posts rest in or near the patient's axillae (armpits). The posts provide a secondary benefit of providing an easy guide for positioning the patient onto the board. The posts may fold down into recesses in the housing during transport and storage of the compression device, and may be raised after a patient has been placed on the board. The posts can raised manually or mechanically.

Figure 7:
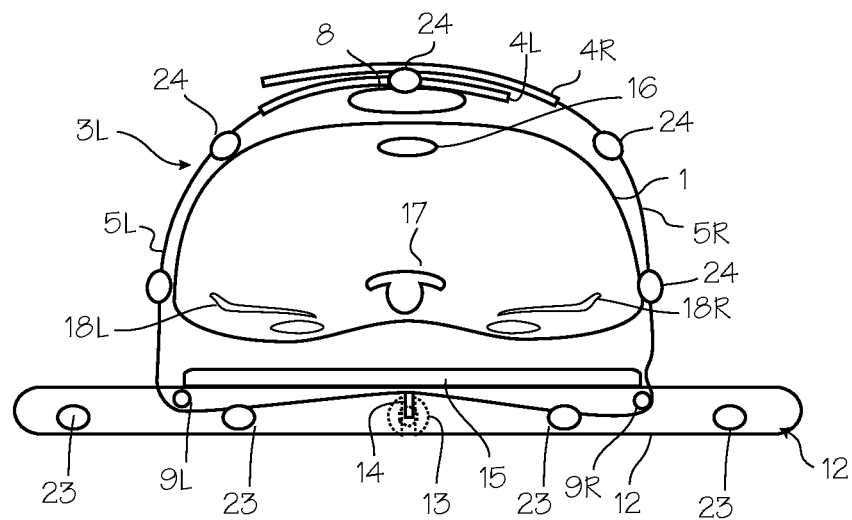
FIG. 7 is a schematic cross section of a chest compression device similar to that of FIG. 3, with one array disposed in the housing of the CPR compression device.

FIG. 7 is a schematic cross section of a chest compression device similar to that of FIG. 3, with one array disposed in the housing of the CPR compression device. In this Figure, the components are similar to the components of the chest compression device of FIGS. 3 and 4, including the compression belt 3L and 3R, the load distribution portions of the belt 4L and 4R, the narrow strap portions 5L and R, the bladder 8, the spindles 9L and 9R, the drive spool 13 and the spline 14 which fixes the belt to the drive spool 15 within the housing 12, and the load plate 15 on the platform. The anatomical landmarks, including the sternum 16, the spine 17, and the right and left scapula 18R and 18L are also shown in the Figure. A first array of emitter/detectors 23 are disposed in or on the housing, and may be dispersed both across the width of the housing (the medial/lateral axis of the patient and the device) and the length or height of the housing (corresponding to the inferior/superior axis of the patient). If necessary, a second array of emitter/detectors 24 are disposed in or on the compression belt, and may be dispersed both across the width of and length of the belt. The emitter/detectors 24 (the array on the belt) would be matched to the emitter/detectors 23 on the housing. Depending on the technology used to implement the distance measurement, emitter/detectors on the belt may used with a corresponding array on the housing, provided that the emitter detectors on the belt can use pre-existing structure on the housing 12, such as the upper surface. Also, depending on the technology used to implement the system, the emitter/detectors 24 can be replaced with detectable markers, or reflectors. Likewise, pre-existing structures on the belt may be used in conjunction with an array of emitter/detectors on the housing to provide the necessary reflective surfaces for some distance sensors.

Figure 8:
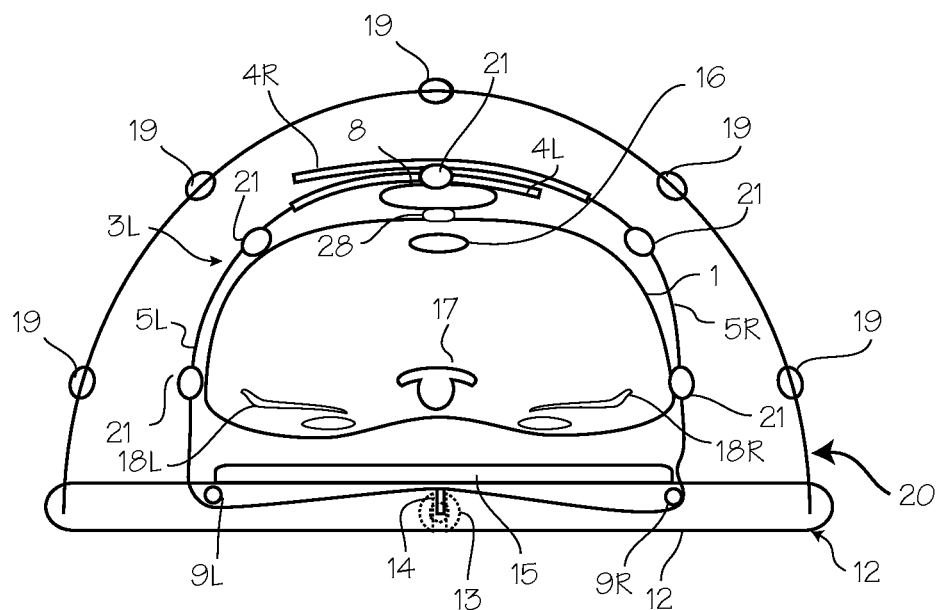
FIG. 8 is a schematic cross section of a chest compression device similar to that of FIGS. 3 through 7, with an additional emitter/detector disposed on the patient's body.

FIG. 8 is a schematic cross section of a chest compression device similar to that of FIGS. 3 through 6, with an additional body-mounted emitter/detector 28 disposed on the patient's body. As with emitter/detectors 21, emitter/detector 28 is interoperable with emitter/detectors 19 or 23 to determine the position of the body-mounted emitter/detector and emitter/detectors fixed relative to the housing. The emitter/detector can be placed directly on the patient, near the sternum and inferior to the bladder 8, and additional body-mounted emitter/detectors can be placed laterally on the patient's rib cage or abdomen. The body-mounted emitter/detector can be incorporated into defibrillator electrode pads, which will typically be placed on the patient before the compression device is applied to the patient. Using the emitter/detector 28 with emitter/detectors 19 or 23, the control system can be operated to detect large undesirable changes in the position of the patient relative to the housing, as might occur during transport of the patient down stairs, over rugged terrain, or in an ambulance.

The detector/emitter system can work on several principles. Non-contact ultrasonic distance sensors (such as those described in U.S. Pat. No. 6,690,616) may be used. In this embodiment, ultrasonic emitter/detectors (components that emit ultrasound and detect ultrasound reflected from nearby objects) are disposed on the support structure. Ultrasonic distance measurement can be accurate to 0.05%. RF Near Object Detection technology can be employed (such as described in U.S. Pub. 2002/0147534). Optical distance sensors can be employed, which use laser emitters and optical detectors which may be closely spaced on the gantry or posts, and direct laser light onto the compression belt surface, or specially applied reflectors and detect the reflected laser light. Magnetic motion sensors, such as those which use an electromagnetic source and sensor, described in Geheb, et al., Method and Apparatus for Enhancement of Compressions During CPR, U.S. Pat. No. 7,220,235 (May 22, 2007) and Centen, et al., Reference Sensor For CPR Feedback Device, U.S. Pub. 2012/0083720 (Apr. 5, 2012), may also be used. These technologies will be sufficient to calculate the depth of compression accomplished by the compression belt.

To determine slippage, or inferior/superior movement of the belt relative to the patient, the arrays can use three detectors on the support structure, where the detectors define a plane (so that they are not arranged in a straight line), and at least one emitter on the compression belt, at a location that most closely conforms to the movement of the chest. Using basic triangulation calculations based on the measured distance from each detector to the emitter, the position of the emitter, and thus the belt, can be calculated. In this manner, a change of the position of the belt-mounted emitter out of the plane established by the three detectors can be interpreted as an inferior/superior movement of the compression belt, or inferior/superior tilting of the belt.

The computer that interprets the data obtained from the sensor arrays is programmed to track motion of the sensors on the belt, and interpret this as belt position. This data can be processed by the computer to determine the depth of compression provided by the belt, and determine superior/inferior motion of the belt during the course of compressions. Upon initiation of the system in a resuscitation attempt, the system will determine the initial position of the belt, relative to the emitter/detectors/markers of the support structure or housing. The system may assume that initial placement is correct, or prompt an operator for confirmation that placement is as desired by the operator. (With addition of an emitter/detector/marker on the belt and the housing, the system can also confirm that the array, belt and housing are all properly aligned on the anterior/posterior axis of the system.) Thereafter, the computer system interprets the data obtained from the arrays, which provide data corresponding to the distance between emitter detectors on corresponding arrays, to determine any inferior/superior drift of the belt. Referring to the additional emitter/detector shown in FIG. 8, the computer is programmed to track motion of the sensors on the support structure or housing, and interpret this as the patient position. This data can be processed by the computer to determine the movement of the patient relative to the support structure or housing. Upon initiation of the system in a resuscitation attempt, the system will determine the initial position of the patient relative to the support structure or housing. The system may assume that initial placement is correct, or prompt an operator for confirmation that patient placement is as desired by the operator. Thereafter, the computer system interprets the data obtained from the arrays, which provide data corresponding to the distance between emitter detectors on corresponding arrays, to determine if the patient has moved relative to the support structure or housing.

In response to detected inferior/superior movement of the belt which exceed a predetermined limit, the computer which controls the CPR compression device can direct operation of the device to take one or more of the following actions: (1) suspend compressions until reset by a CPR provider (2) provide prompts to a CPR provider to indicate the fact that slippage has been detected and/or (3) adjust depth of compression or compression rate, or adjust the compression waveform to account for the slippage while still providing compression. Currently, the predetermined limit for inferior movement (downward movement, relative to the patient's anatomy, such as movement toward the abdomen) should be about 0.5" to 1" (1.25 to 2.5 cm), while the predetermined limit for superior movement (upward movement, relative to the patient's anatomy, such as movement toward the head of the patient) should be about 0.5" to 1" (1.25 to 2.5 cm), for belts used in the AutoPulse® chest compression system. Expressed in terms of the patient's anatomy, motion of a portion of the belt below the xiphoid process, or motion of a portion of the belt above the sternal notch, may be used to establish predetermined limits. Thus, disposing a component of the emitter/detector pair on the superior or inferior edges of the band, or aiming the optical emitter/detector to the superior or inferior edges of the band, and determining the average distance from the edge of the band and the anatomical landmark in the average initial placement of the band, the predetermined limit can be expressed as 0.5" (1.25 cm) below the xiphoid process or above the sternal notch of the patient.

In response to detected compression depth, the computer which controls the CPR compression depth can increase or decrease the amount of compression applied to the patient, by increasing or decreasing the amount of the belt spooled on the drive spool. Also, the computer can direct operation of the device to (1) suspend compressions until reset by a CPR provider (2) provide prompts to a CPR provider to indicate the fact that compression depth is excessive or inadequate and/or (3) adjust depth of compression to accomplish compression to the desired depth of 1.5 to 2 inches (3.75 to 5 cm), and/or (4) adjust the compression wave form or compression rate.

In response to detected displacement of the patient relative to the support structure or housing, the computer which controls the CPR compression depth can direct operation of the device to (1) suspend compressions until reset by a CPR provider and (2) provide prompts to a CPR provider to indicate the fact that unacceptable patient movement has been detected and/or (3) adjust depth of compression to accomplish compression to a depth of lesser than or greater than the recommended 1.5 to 2 inches (3.75 to 5 cm), and/or (4) adjust the compression wave form or compression rate.

Figure 9:
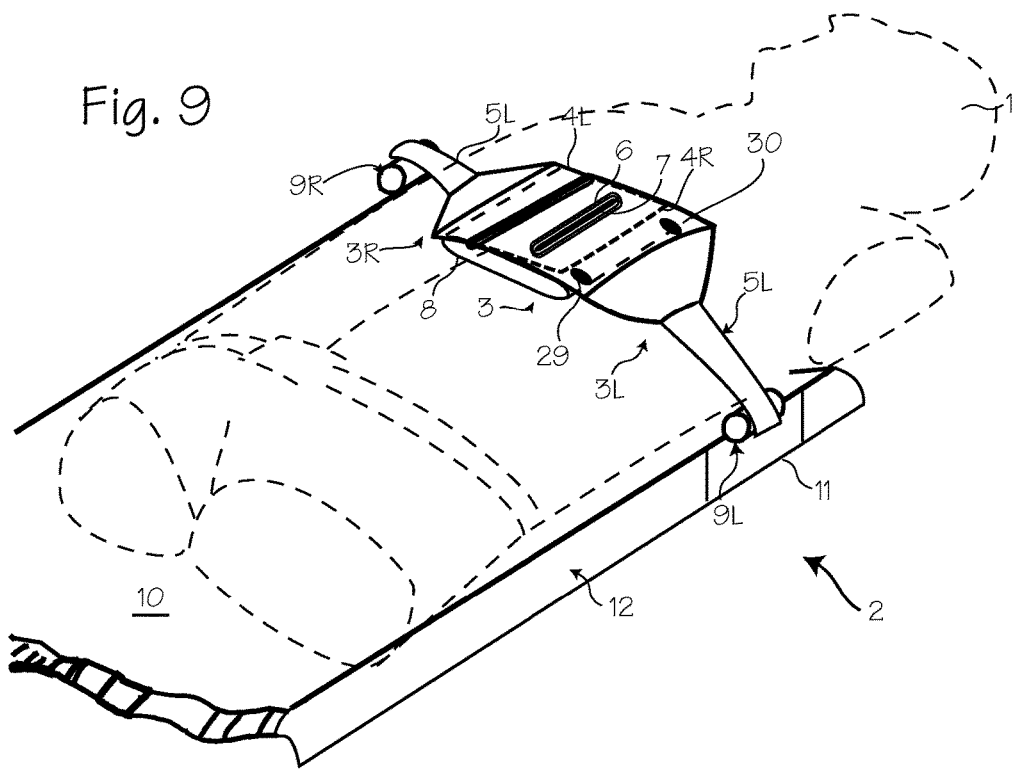
FIG. 9 shows a chest compression belt fitted on a patient.
Figure 10:
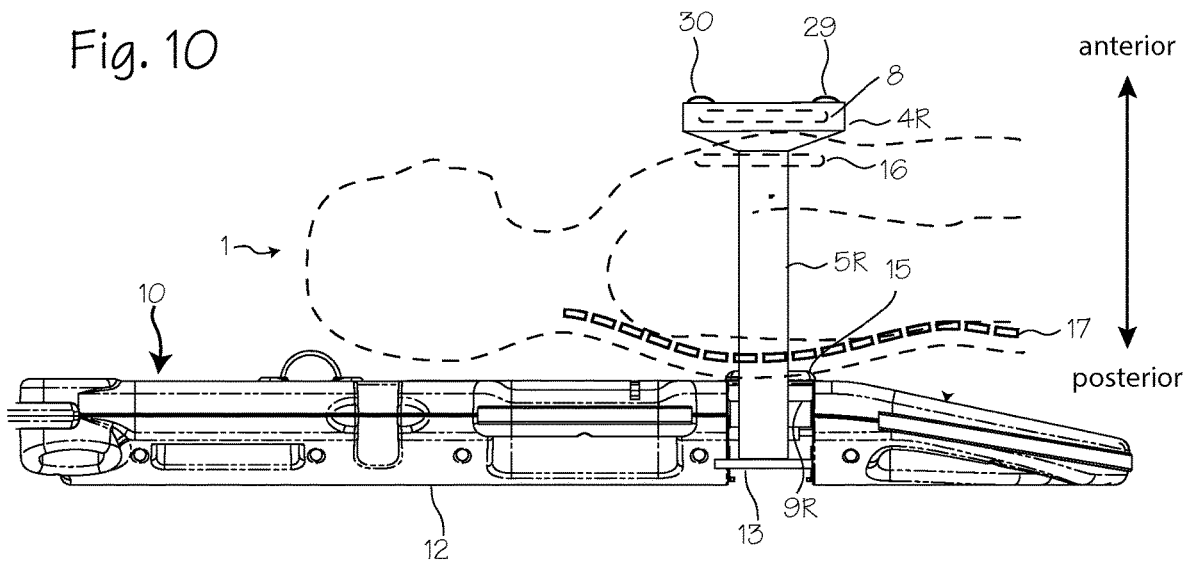
FIG. 10 is a longitudinal cross section of the chest compression device of FIG. 9.

FIGS. 9 and 10 illustrate the chest compression device, similar to the AutoPulse® CPR chest compression device, fitted on a patient 1. The chest compression device 2, belt 3 with right belt portion 3R and a left belt portion 3L, distributing portions 4R and 4L and narrow pull straps 5R and 5L and other components are as described above in relation to FIG. 1. Accelerometers 29 and 30 are disposed on the belt, located along the inferior/superior axis of the belt. As illustrated, the accelerometers are disposed on a load distributing panel. The accelerometers, along with the control system and appropriate programming, can be used to detect acceleration of the belt along the inferior/superior axis and the anterior/posterior axis (as well as the transverse, left-to-right axis) of the patient, and determine the distance traveled by the belt, and different portions of the belt, along both the inferior/superior axis and the anterior/posterior of the axis of the patient. The control system is further programmed such that, upon detection of undesirable movement (either excessive movement or non-uniform movement) the control system operates a display associated with the compression device to warn an operator, and/or suspend compression operation of the device, and/or change the depth of compression and/or adjust the compression wave form or compression rate.

FIG. 10 is a side view of the device of FIG. 9, installed on a patient 1. The components are as describe in relation to the previous Figures, and include the compression belt 3L and 3R, the load distribution portions of the belt 4R and 4L, the narrow strap portions 5R and 5L, the bladder 8, the spindles 9L and 9R, the drive spool 13, the spline 14 and the load plate 15. The anatomical landmarks shown in this Figure include the sternum 16 and the spine 17. Referring to the landmarks, the chest compression band is wrapped around the patient such that the load distributing portions are located on the chest (that is, the anterior surface or portion of the thorax), over the sternum, with the narrow strap portions descending from the load distributing portions to wrap around the lateral spindles and thence run to the drive spool. As described in relation to FIG. 2, the lateral spindles are spaced laterally from the medial centerline of the device so that they are disposed under, or lateral to, the scapulae of the typical patient (see FIG. 2), so that tightening of the compression band results in anterior/posterior compression of the chest.

Figure 11:
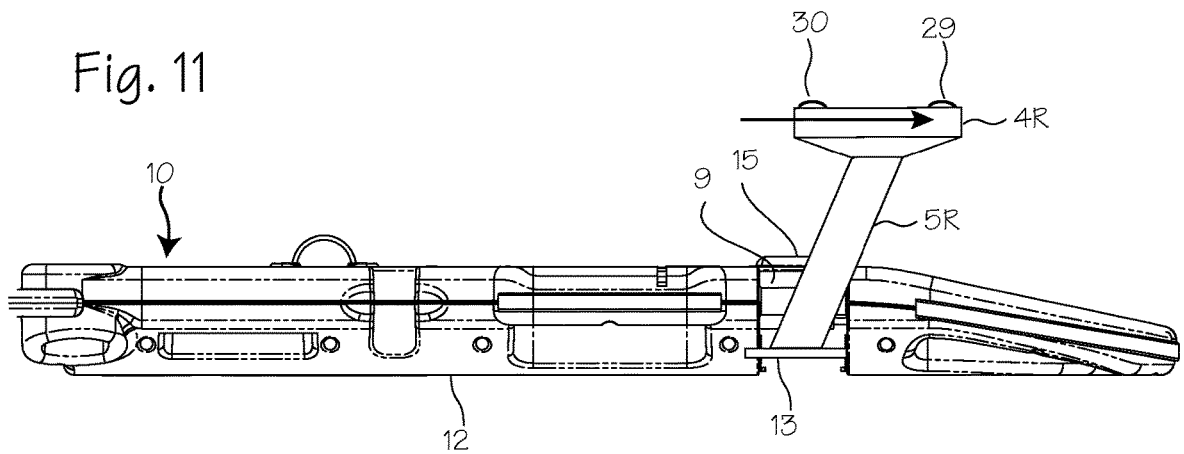
FIG. 11 is a longitudinal cross section of the chest compression device of FIG. 9.
Figure 12:
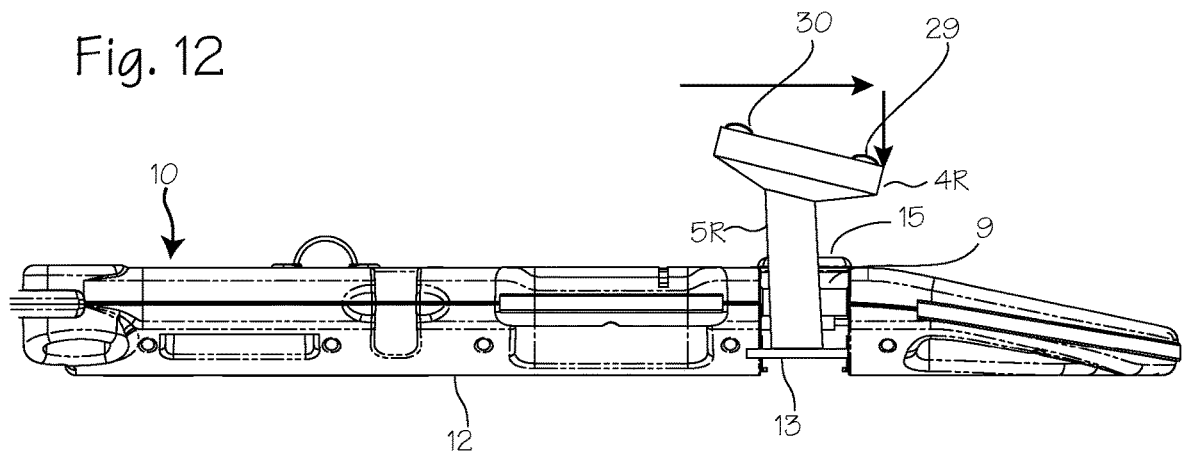
FIG. 12 is a longitudinal cross section of the chest compression device of FIG. 9.

FIGS. 11 and 12 are longitudinal cross sections of the chest compression device of FIGS. 9 and 10, demonstrating the types of belt slippage and movement that the system is intended to detect. In FIG. 11, the belt has moved horizontally, along the inferior/superior axis of the housing and the patient. This horizontal movement is undesirable, because the system assumes that the patient is positioned relative to the housing such that the load distributing portion of the belt, when in its original position centered over the drive spool and load plate, is also properly located over the chest (the anterior surface of the thorax) of the patient, and thus the narrow strap portions of the belt are aligned vertically (as close a possible to vertically) so that the tension applied through the narrow straps is directed substantially entirely along anterior/posterior axis (front to back, or straight downward when installed on a supine patient), rather than pulling inefficiently along the inferior/superior axis.

In FIG. 12, the belt, and specifically the load distributing portion of the belt, has become tilted upon tightening of the belt, in the sense that the inferior extent of the load distributing portion moves further downward during a compression than does the superior extent of the load distributing portion. Extreme non-symmetrical movement of the belt is undesirable because it is unexpected assuming that the belt is properly positioned such that the load distributing portion of the belt, when in its original position centered over the drive spool and load plate, is also properly located over the chest (the anterior surface of the thorax) of the patient, so that the load distributing portion is disposed over the sternum and acts on the patient's rib cage. Extreme non-uniform or non-symmetrical anterior-to-posterior movement of the belt, in the sense that the top (superior portion) of the belt moves posteriorly either more or less than the bottom (inferior portion) may be a sign that the belt has moved, relative to the patient, such that the inferior portion is impinging on the patients abdomen, or that the belt is encountering some interference. It could also be a sign that the patient's thorax has changed significantly in its response to compressions. Changes could be due to rib breakage, sternum breakage, or normal response to repeated chest compressions.

Using the techniques disclosed in our prior patents for determining chest compression depth with or without reference to fixed reference sensors, the accelerometers can readily be used to provide acceleration data regarding horizontal inferior/superior movement of the belt and/or transverse motion of the belt. Using readily available three-axis accelerometers, chest compression depth at various points long the inferior/superior axis of the belt can also be determined.

With an accelerometer fixed to the load distributing portion of the belt, preferably near the centerline of the patient, an accelerometer signal corresponding to the inferior/superior position of the belt, relative to its initial placement, can be obtained. Because use of the CPR chest compression device requires human operators for placement and initiation of the system, the initial position of the belt can be assumed to be a correct position, and the position detecting system can be used to monitor movement using the stationary accelerometer data upon startup as a starting point for calculating movement. Alternatively, because we are concerned with motion of the belt relative to the patient's chest, and assume that the patient is substantially fixed relative to the housing, a reference accelerometer disposed on the housing can also be used to detect overall movement of the housing, and the signals of the housing mounted accelerometer and the belt-mounted accelerometer may be combined (subtracted) to determine movement of the belt vis-à-vis the housing.

To detect inferior/superior movement of the belt, the accelerometer is coupled to the compression belt with an axis of acceleration sensitivity (the term of art used by accelerometer makers) aligned with the inferior/superior axis of the belt (which corresponds to the inferior/superior axis of the housing and the patient). To detect anterior/posterior movement of the belt, the accelerometer is coupled to the compression belt with an access of acceleration sensitivity (the term of art used by accelerometer makers) aligned with the anterior/posterior axis of the belt (which corresponds to the anterior/posterior axis of the housing and the patient). If a three-axis accelerometer (that is, three accelerometers arranged orthogonally, within a single device) is used, the remaining axes can be used also, to provide acceleration data related to left to right motion, of the belt. An Analog Devices ADXL345 three-axis digital accelerometer, which is used in our PocketCPR® device, may be used in the device described here, and an Analog Devices ADXL321 two-axis accelerometer, or two ADXL103 single-axis accelerometers may also be used. The inferior/superior accelerometer is operated to provide acceleration signals to the microprocessor (the computer used to interpret the acceleration data may be the same computer that controls the chest compression operation of the device, or a separate microprocessor or computer), and the control system is programmed to calculate, based on the acceleration signal, the inferior/superior distance over which the accelerometer moves from its original location. The anterior/posterior accelerometer is operated to provide acceleration signals to the microprocessor (the computer used to interpret the acceleration data may be the same computer that controls the chest compression operation of the device, or a separate microprocessor or computer), and the control system is programmed to calculate, based on the acceleration signal, the anterior/posterior distance over which the accelerometer moves from its original location. (While it is preferred to align the axes of acceleration sensitivity with the axes of the patient, it is not necessary, but the acceleration signal provided by the accelerometer is strongest along its axis of acceleration sensitivity. Misalignment can be accounted for through calculations to obtain suitable distance determinations.)

Upon initiation of the chest compression device, the accelerometer should be stationary in the inferior/posterior plane and the anterior/posterior plane, and thus the accelerometer(s) should be outputting a signal indicating zero acceleration and velocity. Prior to initiation of compressions, the control system, through the display on the device, or through a speaker, prompts the user to confirm proper placement of the belt. Upon user input (push of a start button (physical or touch screen) or keyboard command, or other input), the control system initiates compression belt operation to accomplish a series of repeated tightening and loosening of the belt about the thorax of the patient. The control system is programmed with the assumption that this position is an acceptable position of the belt, and thus the accelerometer. The control system is programmed to compare the measured inferior/posterior distance to a predetermined distance, or distances, and provide output depending on how far the belt has moved in the inferior/posterior axis. The control system is programmed to provide output, depending on the calculated distance, to the CPR provider, or to other components of the system, and is also programmed to control operation of the belt in response to the determined distance.

For example, upon detection of slight slippage, which is inevitable and not of concern (in the range of 1 to 2 cm), the control system can operate the display on the platform to provide a visual display element, including text or an icon, to indicate that the belt inferior/posterior position is within a nominal range of deviation from the original position.

Upon detection of significant inferior/posterior movement, which exceeds the nominal range of movement but is not presumptively a sign of defective operation, the control system operates the display to provide a visual display element, or operate a speaker to provide an audible prompt, indicating that the belt has moved a sufficient distance to warrant inspection and confirmation that the belt is still appropriately placed.

Upon detection of excessive inferior/posterior movement, which exceeds the nominal range to the degree that it is presumptively a sign of unacceptable slippage of the belt toward the abdomen or throat of the patient, the control system is programmed to operate the display to provide a visual display element, or operate a speaker to provide an audible prompt, to communicate to the operator that significant inferior/posterior movement has been detected. Additionally, the control system is programmed to stop operation of the belt tensioning mechanisms and return the system to a safe state, such as complete relaxation of the belt. The control system may also be programmed to take intermediate steps, such as adjusting the depth of compression to accomplish compression to a depth lesser than or greater than the recommended 1.5 to 2 inches (3.75 to 5 cm), and/or (4) adjust the compression wave form or compression rate.

Upon detection of excessively asymmetrical or non-uniform anterior/posterior movement, which exceeds the nominal range to the degree that it is presumptively a sign of unacceptable non-uniformity of the downward motion of the belt, the control system is programmed to operate the display to provide a visual display element, or operate a speaker to provide an audible prompt, to communicate to the operator that significant non-uniform motion has been detected. Additionally, the control system may be programmed to stop operation of the belt tensioning mechanisms and return the system to a safe state, such as complete relaxation of the belt. The control system may also be programmed to take intermediate steps, such as adjusting the depth of compression to accomplish compression to a depth lesser than or greater than the recommended 1.5 to 2 inches (3.75 to 5 cm), and/or (4) adjust the compression wave form or compression rate.

Upon detection of significant non-uniformity of the downward motion of the belt, which exceeds the nominal range of movement but is not presumptively a sign of defective operation, the control system is programmed to operate the display to provide a visual display element, or operate a speaker to provide an audible prompt, indicating that the belt attained a non-uniform downward movement significant to warrant inspection and confirmation that the belt is still appropriately placed that the system is operating properly and the patient is responding as expected.

For both slip detection and non-uniformity detection, the control system of the device can be programmed to control operation of the belt in response to the detected movement of the belt, and to control operation of any associated display or audio output to provide various advisory outputs in addition to those mentioned above. For horizontal slip detection, only a single accelerometer is needed. For detection of non-uniform downward movement, two or more accelerometers may be used. When more accelerometers are used, a finer determination of the shape of the chest during compression can be obtained.

The systems have been described in the context of the CPR compression device similar to the AutoPulse® CPR compression device which uses the load distributing band, with emphasis on detection of slippage. The arrays can also be applied to other automated or motorized chest compression belt systems, such as the system proposed in Lach, Resuscitation Method and Apparatus, U.S. Pat. No. 4,770,164 (Sep. 13, 1988). Also, the device is illustrated with the commercially implemented drive spool and motor as the means for tightening the belt about the chest and thorax of the patient. The system described above can be used with this and any other means for tightening the belt about the chest and thorax of the patient, including the numerous mechanisms disclosed in Lach and related patents such as Kelly, Chest Compression Apparatus for Cardiac Arrest, U.S. Pat. No. 5,738,637.

Figure 13:
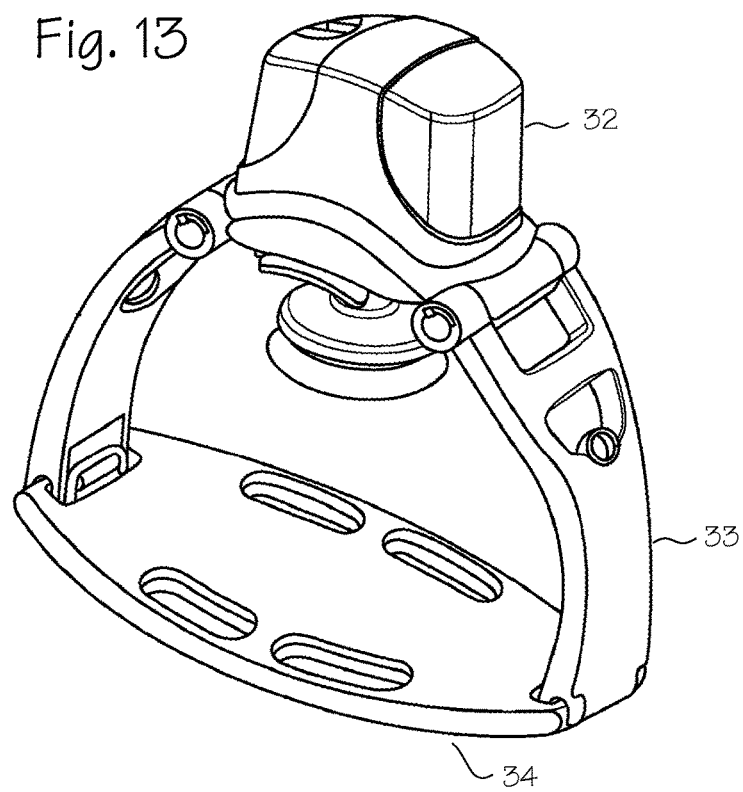
FIGS. 13 and 14 illustrate the application of the system of motion detection applied to a piston based chest compression device.
Figure 14:
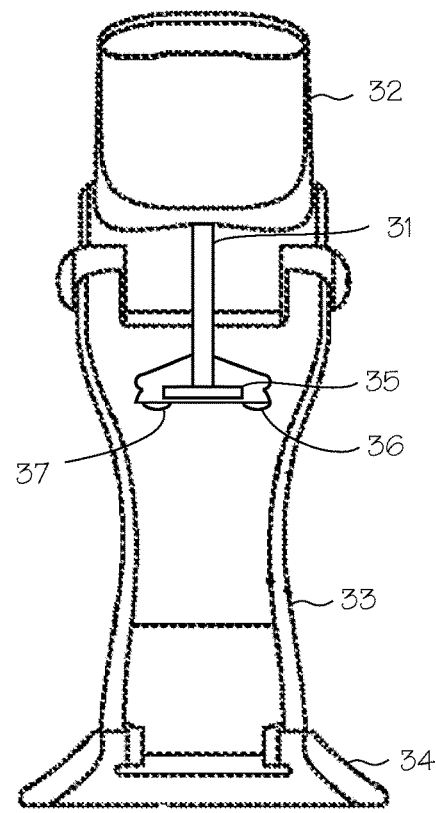

In the LUCAS™ system (described in U.S. Pat. No. 7,569,021), the piston is rigidly locked in place relative to the back plate, so like the system of FIGS. 3 and 4, a support structure which is fixed relative to the base structure of the patient can be used to support one of the arrays. The rigid legs described by U.S. Pat. No. 7,569,021 may be used as the support structure for the array. The necessary markers or corresponding second emitter/detector array can be placed on the patient's chest, in an electrode assembly the will be used for defibrillation, or in a separate array, or on the outer edge of the piston itself. The system can be applied to piston-based systems, such as the LUCAS™ CPR chest compression system, to detect undesired tilt of the system during use, or migration of the piston relative to the target area of the sternum. This application is illustrated in FIGS. 13 and 14 which show the LUCAS™ system in which a piston 31 and piston driving mechanism 32 are suspended on support arms 33, and the support arms are fixed to a rigid backboard 34. The space between the piston and the backboard accommodates a cardiac arrest patient. When initially installed on a patient, the piston is aligned vertically, and the compression pad 35 lower surface, which impinges upon the chest of the patient, is horizontal. The entire device is subject to tilting after initial placement. With accelerometers mounted on the compression pad, with the accelerometers disposed along the inferior/superior axis, for example with one accelerometer 36 (FIG. 14) disposed inferiorly to a second accelerometer 37, each with an axis of sensitivity aligned with the inferior/superior axis and the anterior/posterior axis, the control system can determine the orientation of the compression pad and determine whether the compression pad has deviated from its original horizontal orientation, and control the device or an associated display or audio output in a manner similar to that described above in relation to the compression belt system. A deviation from horizontal orientation can be determined based on acceleration data regarding upward and downward movement of the accelerometers (and, hence, the inferior and superior portions of the compression pad). A deviation greater than 5° (degrees of departure from horizontal) from the orientation upon initiation of the system, determined by comparing the downward distance traversed by each accelerometer (calculated from the acceleration signal), would, for example, result in operation of the control system to present warnings to an operator, while deviation greater than 10° would result in operation of the control system to suspend compressive operation of the piston.

Figure 15:
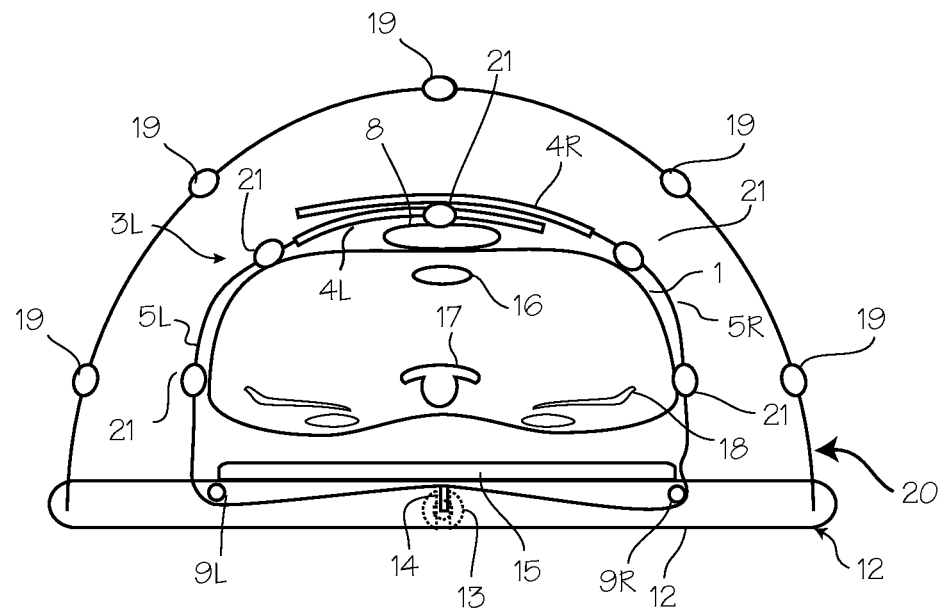
FIGS. 15 and 16 illustrate the application of the chest compression device to patients with varying thoracic cross-sections.
Figure 16:
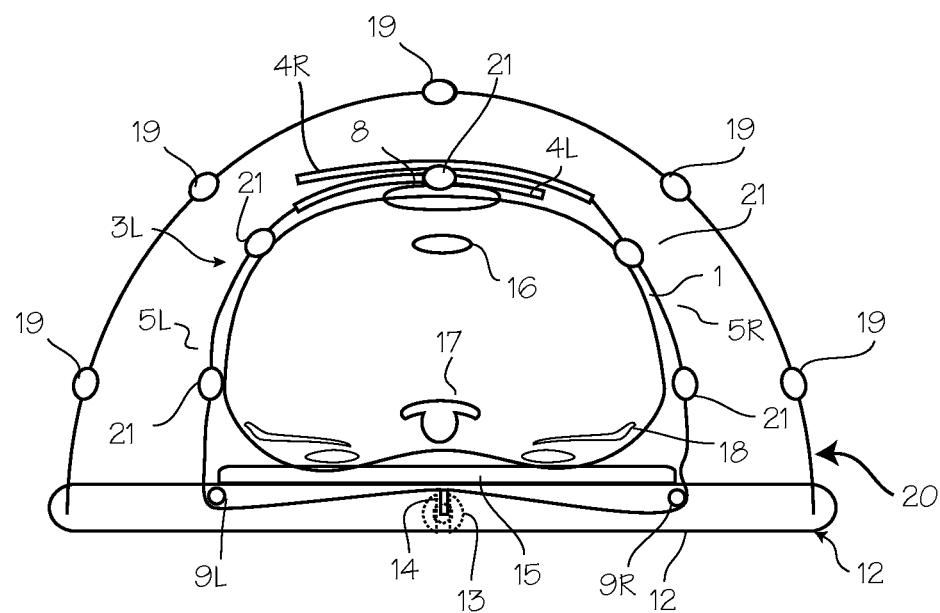

Referring again to the embodiments of FIGS. 3, 4, 5, 6 and 7, these devices can be used to implement a method of controlling the automated chest compression devices based on the initial shape of the patient and on changing compliance of the patient over an extensive course of CPR compressions. Some patients have relatively flat ribcages, as illustrated in FIG. 15, while other patients are barrel chested, and have relatively round ribcages, as shown in FIG. 16. The barrel chested patient may require deeper compressions than the flat chested patient, and the flat chested patient may be successfully revived, with lower risk of iatrogenic injury, with more shallow chest compressions (vis-à-vis the barrel chested patient or the average patient). Accordingly, the chest compression devices of FIGS. 15 and 16 include all the components of the devices of FIGS. 3 and 4, or FIGS. 5, 6 and 7 and can be operated, through the computerized control system, to determine the initial shape of the patient's shape by measuring the distance from the gantry or backboard emitter/detectors 19 and associated emitter/detectors 21 on the compression belt 3. The control system is programmed to calculate the general shape of the patient disposed within the belt, and thereafter operate the compression belt to provide compressions of differing extent dependent on the general shape of the patient (as computed from input from the sensors). (Our prior U.S. Pat. No. 6,616,620 provided for adjusting the compression depth achieved by the system based on the circumference of the patient, as determined by calculating the paid out length of the belt after slack take-up). The control system may be programmed to determine the anterior/posterior thickness of the patient's chest, and determine whether the patient is barrel chested, normal, or flat-chested, based on the anterior/posterior thickness of the patient's chest. For a more rigorous analysis, the control system can be programmed to determine the actual shape of the anterior surface of the chest, and determine that the patient is typical or barrel-chested based on the calculated shape of the patient's chest.

For example, a generally accepted goal for compression depth is 1.0 to 2.0 inches (2.5 cm to 5 cm). For patients with unusually round thorax, that goal can be adjusted to 1.5 to 2.5 inches (4 cm to 6.4 cm). This is accomplished by programming the control system to operate the motor so as to spool more of the belt during compressions strokes, upon detection of a barrel chested patient.

Figure 17:
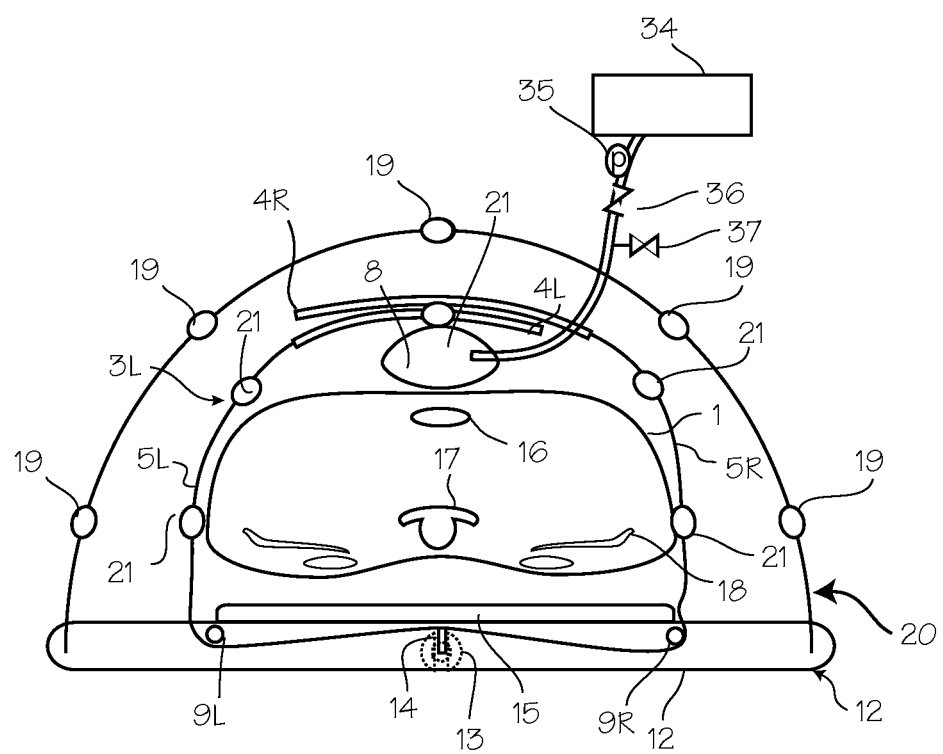
FIG. 17 illustrates use of the chest compression device in combination with the distance sensors and an adjustable bladder disposed between the compression belt and the patient.

In addition to altering the depth of compression achieved during the compression stroke, the control system can also be programmed to adjust the initial shape of the bladder (item 8 in Figures) upon detecting a thoracic shape, such as a flat thorax shown in FIG. 15. FIG. 17 illustrates use of the chest compression device in combination with the distance sensors and an adjustable bladder disposed between the compression belt and the patient. In this system, the bladder is operated in a static mode (that is, it is not cyclically inflated in a dynamic manner to cause chest compressions, but is filled and/or inflated prior to compressions and thereafter maintains a static volume (excepting minimal leakage and some slight compression) that modifies the forces applied by the compression belt). Adjustment of the initial shape of the bladder can be accomplished by providing a pump 38, a pressure sensor 39 in fluid communication with the bladder and/or pump and a check valve at the outlet of the pump and a vent valve for deflating the bladder when desired. The operation of the pump, check valve 40 and vent valve 41 can all be controlled by the control system in response to the data derived from the emitter/detectors and the pressure sensor. As an example, for patients of average size and shape, the bladder may be used as described in U.S. Pat. No. 6,616,620, as a static bladder of a generally flat configuration when relaxed. For patients with a more shallow thorax, the bladder may be inflated to a cylindrical shape, extending the combined height of the bladder and the patient's chest (most conveniently, co-extensive with the chest compression belt or load distributing panels of the load distributing band).

The method of operation can be applied to patient in a piston system, such as that shown in FIGS. 13 and 14, with the addition of an array of emitter/detectors on the patient and the gantry of the piston-based compression device. Control systems may be employed with these piston-based systems analyze sensor input, calculate patient shape, and operate the piston to achieve compressions to a depth dependent on the patient shape, according to predetermined parameters of patient shape.

Referring back to FIGS. 9 and 10, the chest compression device fitted with accelerometers to detect slippage can also be augmented to determine changes in chest compliance versus depth of compression. When the chest becomes excessively compliant, this the compressions may have cracked the patient's ribs or sternum. While fractures are a necessary and acceptable incident of CPR, the effectiveness of CPR may decrease if the number of fractures degrades the resiliency of the chest. Accordingly, it may be desirable to decrease the force and depth of automated compressions when the resilience of the chest drops. To detect a drop in chest wall resilience, the pressure applied by the device to the chest, or some proxy, such as pressure in the bladder, or pressure in additional bladders, may be monitored and compared to the measured compression depth. When compressing a patient with an intact rib cage, the initial pressure/depth ratio should be relatively high. If several ribs are broken during the course of CPR, the pressure needed to compress to the desired depth should decrease abruptly.

Figure 18:
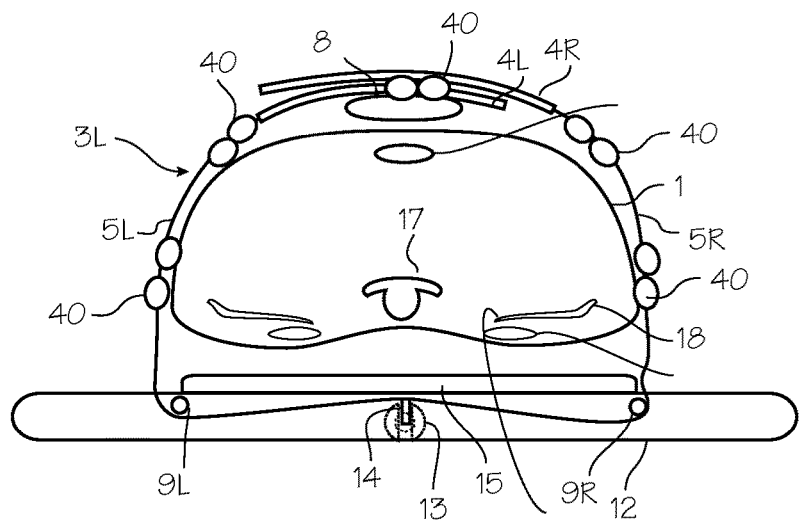
FIG. 18 illustrates a system similar to that of FIGS. 9 and 10, with the additional features to detect changes in chest resilience.
Figure 19:
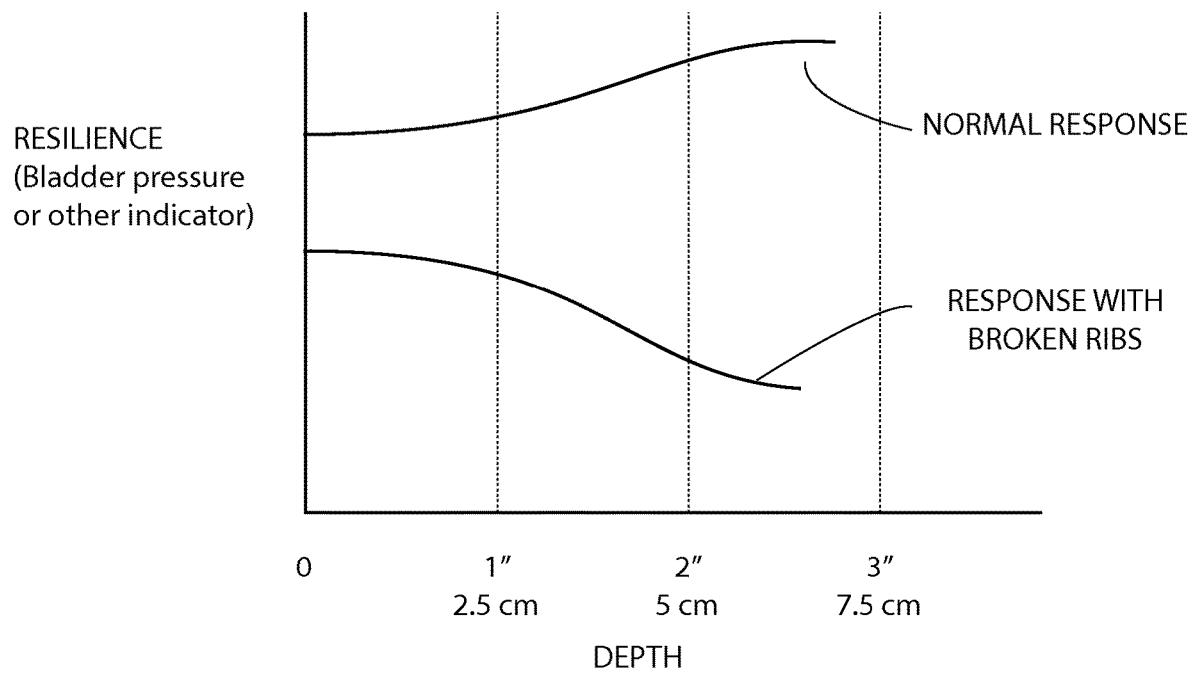
FIG. 19 is a graph illustrating the relationship between chest resilience and compression depth.

FIG. 18 illustrates a system similar to that of FIGS. 9 and 10, with the additional features to detect changes in chest resilience. The system can detect the pressure applied to the chest by detecting the pressure in the bladder 8 or additional bladders 42 disposed on the compression belt. Other means for detecting the force applied to the chest, or the resistance provided by the chest to further compression, including the load cell disclosed in U.S. Pat. No. 7,270,639, disposed under the back of the patient, torque sensors operably attached to the motor that drives the system, and strain gauges in the belt, piezo-electric sensors in the belt, and other suitable sensors, can be used in place of pressure sensors. FIG. 19 is a graph illustrating the relationship between chest resilience and compression depth. The upper curve illustrates the expected relationship between chest resilience versus compression depth. As expected, chest resilience (as indicated by bladder pressure or other indicator, is significant at the start of a compression, and increases with the depth of the compression. This is shown in the upper curve. Over the course of many compressions, chest resilience is expected to drop, but excessive loss of resilience such as that illustrated in the lower curve should be addressed by the system or an operator.

Through the use of multiple pairs of pressure and displacement sensors, resilience can be measured at multiple locations along the extent of the interface between the load distributing band and the patient surface. This is important as force is also distributed along the inferior/superior length of that interfacial surface, and rib fractures occur at specific locations along the ribs. Multiple sensors will allow for a more precise localization of where the fracture occurs, which in itself may be helpful to the rescuer, or may provide information for the control system which may be programmed to adjust the compression parameters to maximize hemodynamics whilst minimizing injury to that specific fracture location. This may be accomplished by having multiple inflatable bladders on the compression belt that can be inflated or deflated to alleviate undue pressure to that particular injury location.

To address this issue of a decrease in chest wall resilience, and continue providing effective compressions, the control system can decrease the applied compression force, and decrease the spooling of the belt to achieve a lesser compression depth, when a fall-off of resistance v. depth change is detected. Thus, for example, peak bladder pressure of 2 psi (0.138 bar) may be normal, especially at the start of compressions. With the compression device operating normally to achieve 2 inches (5 cm) of compression depth, a drop off of peak bladder pressure to 1 psi (0.069 bar) might indicate a change in chest resilience due to broken ribs. The baseline resilience for a particular patient is calculated at the initiation of compressions, with monitoring for changes over time. The numbers expressed above are merely illustrative. The control system can be programmed such that, if such a change is detected by the pressure sensors and the control system, the control system may operate the compression belt to provide a lesser depth of compression, such as 1.1 inches (2.8 cm). This will provide adequate compressions, though less than ideal, which will limit further rib fractures which would make continued compressions at any level ineffective. The control system can also be programmed such that, if broken ribs are detected, the control system may operate the compression belt to accomplish the compression stroke over a longer time period, which would lead to lower compression velocity and minimize risk of further fractures. The compression stroke could be lengthened from the currently preferred 200 milliseconds to 300 milliseconds, and the compression rate could be lowered from the preferred 80 compression per second to 50-60 compressions per minute.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A system for performing cardiopulmonary resuscitation (CPR) on a patient, the system comprising:
    a housing providing a platform adapted to be disposed under a thorax of the patient during CPR;
    an automated chest compressor coupled to the housing and configured to provide chest compressions to the patient;
    two or more sensors attached to the automated chest compressor and configured to generate data indicative of movement of at least a portion of the automated chest compressor relative to the thorax of the patient; and
    a controller configured to:
        instruct the automated chest compressor to compress the thorax of the patient at a resuscitative rate and depth,
        receive the data indicative of the movement of the at least a portion of the automated chest compressor,
        calculate a positioning of the at least a portion of the automated chest compressor relative to the thorax of the patient based on the received data,
        detect the movement of the at least a portion of the automated chest compressor along an inferior/superior axis relative to the thorax of the patient based on the calculated positioning; and
    an output device communicatively coupled to the controller that provides feedback based on the detected movement of the at least a portion of the automated chest compressor along the inferior/superior axis relative to the thorax of the patient.

2. The system of claim 1, wherein the output device is communicatively coupled to the controller and configured to provide alerts in response to the detected movement of the at least a portion of the automated chest compressor along the inferior/superior axis relative to the thorax of the patient by the controller.

3. The system of claim 2, wherein upon detection of the movement of the at least a portion of the automated chest compressor along the inferior/superior axis relative to the thorax of the patient, the controller is further configured to implement at least one of: (i) suspend compressions of the automated chest compressor (ii) adjust a depth of compression and/or a rate of compression of the automated chest compressor, and (iii) adjust a compression waveform to account for the detected movement of the at least a portion of the automated chest compressor along the inferior/superior axis relative to the thorax of the patient.

4. The system of claim 1, wherein the detection of the movement of the at least a portion of the automated chest compressor along the inferior/superior axis relative to the thorax of the patient comprises detection of the movement of the at least a portion of the automated chest compressor along the inferior/superior axis relative to the thorax of the patient exceeding a predetermined limit.

5. The system of claim 4, wherein the controller is further configured to calculate an amount of the movement of the at least a portion of the automated chest compressor along the inferior/superior axis relative to the thorax of the patient based on the received data from the two or more sensors.

6. The system of claim 5, wherein the controller is further configured to compare an amount of the movement to a predetermined value to determine whether the amount of the movement exceeds a nominal range of an amount of a movement.

7. The system of claim 6, wherein the nominal range of the amount of the movement is between approximately 1.25 centimeters and 2.5 centimeters.

8. The system of claim 1, wherein the automated chest compressor comprises a compression belt and a belt tensioner configured to tighten the compression belt around the thorax of the patient in order to compress the thorax of the patient at the resuscitative rate, and the at least a portion of the automated chest compressor comprising at least a portion of the compression belt.

9. The system of claim 1, wherein the two or more sensors include at least one of optical emitters, ultrasound emitters, and Radio Frequency Identification (RFID) emitters.

10. The system of claim 1, wherein the housing comprises at least 3 three detectors to detect signals being generated by the two or more sensors, and the controller is configured to perform a basic triangulation to determine a change of position of the at least a portion of the automated chest compressor relative to the thorax of the patient.

11. The system of claim 1, wherein the two or more sensors comprise at least two three accelerometers.

12. The system of claim 11, wherein the at least three accelerometers comprise three-axis accelerometers.

13. The system of claim 1, wherein the controller is further configured to detect the movement of the at least a portion of the automated chest compressor exceeding a predetermined limit in response to the received data indicative of the movement of the at least a portion of the automated chest compressor.

14. The system of claim 13, wherein the controller is further configured to generate one or more prompts to a CPR provider to indicate that the movement of the at least a portion of the automated chest compressor exceeding the predetermined limit is detected.

15. The system of claim 1, wherein the automated chest compressor is a piston-based system that comprises:
    a piston,
    a support structure, which includes arms for supporting the piston and a piston driver, and
    a compression pad that is affixed to the piston.

16. The system of claim 15, wherein the controller is configured to detect migration of the piston relative to a target area of the thorax of the patient, the migration being indicative that the piston has moved toward the patient's abdomen or head during the chest compressions.

17. The system of claim 15, wherein the two or more sensors comprise two or more accelerometers that are affixed to the piston and generate acceleration data.

18. The system of claim 17, wherein the controller detects a deviation from a horizontal orientation based on changes in the acceleration data from the two or more sensors affixed to the piston, said deviation being an indication of a migration of the piston relative to a target area of the thorax of the patient.

19. The system of claim 18, wherein upon detection of the deviation of greater than five degrees from the horizontal orientation, the controller generates an audible or visual warning for presentation by the output device.

20. The system of claim 19, wherein upon detection of the deviation of greater than 10 degrees from the horizontal orientation, the controller suspends operation of the piston.

21. The system of claim 1, wherein the controller is configured to detect migration of the at least a portion of the automated chest compressor relative to a target area of the thorax of the patient, the migration being indicative that the at least a portion of the automated chest compressor has moved toward the patient's abdomen or head during the chest compressions.

22. The system of claim 2, wherein the output device includes at least one of visual feedback on a display or audible feedback on a speaker.

23. The system of claim 8, wherein the controller is configured to detect a migration of the at least a portion of the compression belt relative to a target area of the thorax of the patient, wherein the migration is due at least in part to slippage of the at least a portion of the compression belt.

24. The system of claim 15, wherein the two or more sensors comprise three or more accelerometers that are affixed to the piston and generate acceleration data.

25. The system of claim 8, wherein the movement of the at least a portion of the compression belt of the automated chest compressor along the inferior/superior axis relative to the thorax of the patient is due at least in part to slippage.

26. The system of claim 25, wherein the slippage is caused at least in part by force applied on the patient during the chest compressions.

27. The system of claim 25, wherein the slippage is caused at least in part by a change of shape of the thorax of the patient during the chest compressions.

28. The system of claim 25, wherein the controller is configured to detect movement of the at least a portion of the compression belt along an anterior/posterior axis relative the thorax of the patient.

29. The system of claim 25, wherein the controller is configured to detect movement of the at least a portion of the compression belt along a transverse axis relative the thorax of the patient.

30. The system of claim 1, wherein the at least a portion of the automated chest compressor is a chest compression belt of the automated chest compressor.

31. The system of claim 1, wherein the at least a portion of the automated chest compressor is a piston of the automated chest compressor.

* * * * *

UNITED STATES PATENT AND TRADEMARK OFFICE
CERTIFICATE OF CORRECTION

| | |
|---|---|
| PATENT NO. | : 10,918,566 B2 |
| APPLICATION NO. | : 15/891639 |
| DATED | : February 16, 2021 |
| INVENTOR(S) | : Ulrich Herken et al. |

It is certified that error appears in the above-identified patent and that said Letters Patent is hereby corrected as shown below:

In the Specification

Column 1, Line 8, after "Application" insert --No.--

In the Claims

Column 18, Line 61, after "least" delete "3"

Column 18, Line 67, after "least" delete "two"

Column 20, Line 30, after "relative" insert --to--

Column 20, Line 34, after "relative" insert --to--

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*